United States Patent
Tessier

(10) Patent No.: US 11,851,487 B2
(45) Date of Patent: Dec. 26, 2023

(54) METHODS AND SYSTEMS FOR DETECTING PEPTIDE AGGREGATES

(71) Applicant: Rensselaer Polytechnic Institute, Troy, NY (US)

(72) Inventor: Peter M. Tessier, Ann Harbor, MI (US)

(*) Notice: Subject to any disclaimer, the term of this patent is extended or adjusted under 35 U.S.C. 154(b) by 464 days.

(21) Appl. No.: 16/541,939

(22) Filed: Aug. 15, 2019

(65) Prior Publication Data

US 2020/0308273 A1  Oct. 1, 2020

Related U.S. Application Data

(60) Provisional application No. 62/827,496, filed on Apr. 1, 2019.

(51) Int. Cl.
  *C07K 16/26* (2006.01)
  *G01N 33/74* (2006.01)
  *G01N 33/68* (2006.01)

(52) U.S. Cl.
  CPC ......... *C07K 16/26* (2013.01); *G01N 33/6854* (2013.01); *G01N 33/74* (2013.01); *C07K 2317/622* (2013.01); *G01N 2333/605* (2013.01)

(58) Field of Classification Search
  CPC .............. C07K 16/26; C07K 2317/622; G01N 33/6854; G01N 33/74; G01N 2333/605
  See application file for complete search history.

(56) References Cited

U.S. PATENT DOCUMENTS

| | | | | |
|---|---|---|---|---|
| 2004/0052766 A1* | 3/2004 | Solomon | ................ | C07K 14/47 424/93.2 |
| 2009/0232733 A1* | 9/2009 | O'Nuallain | ............ | C07K 16/18 424/1.49 |
| 2010/0202968 A1* | 8/2010 | Nitsch | ..................... | A61P 25/08 424/9.1 |

OTHER PUBLICATIONS

Vajdos et al. (J. Mol. Biol. 2002, Jul. 5, 320(2):415-28 at 416) (Year: 2002).*

* cited by examiner

Primary Examiner — Changhwa J Cheu
(74) Attorney, Agent, or Firm — Murtha Cullina LLP; Anthony P. Gangemi

(57) ABSTRACT

Provided herein are conformation-specific antibodies which bind to protein aggregates, such as amyloid fibrils, including aggregates of glucagon and liraglutide. Also provided are methods of using the antibodies to detect protein aggregates in samples, and methods for identifying aggregate-binding antibodies.

8 Claims, 7 Drawing Sheets

Specification includes a Sequence Listing.

| Kabat # | 47 | 48 | 49 | 50 | 51 | 52 | 52A | 53 | 54 | 55 | 56 | 57 | 58 | 59 | 60 | 61 | |
|---|---|---|---|---|---|---|---|---|---|---|---|---|---|---|---|---|---|
| Codon | TGG | RTK | KST | DBG | ATT | WMT | BMT | DVC | RRC | RGC | DMT | AYC | NRC | TAT | GYT | GAT | |
| Initial library members | Trp | Val<br>Met<br>Ile | Gly<br>Ser<br>Ala<br>Cys | Arg<br>Trp<br>Gly<br>Val<br>Ser<br>Ala<br>Leu<br>Met<br>Thr | Ile | Tyr<br>Ser<br>Asn<br>Thr | Pro<br>Tyr<br>Ser<br>Ala<br>Asp<br>His | Thr<br>Ser<br>Asp<br>Tyr<br>Asn<br>Ala<br>Cys<br>Gly | Asn<br>Gly<br>Ser<br>Asp | Gly<br>Ser | Tyr<br>Ser<br>Asn<br>Thr<br>Asp<br>Ala | Thr<br>Ile | Arg<br>Tyr<br>Asn<br>Asp<br>Cys<br>Gly<br>His<br>Ser | Tyr | Ala<br>Val | Asp | |
| 1 | W | I | G | T | I | N | P | N | N | S | Y | I | D | Y | V | D | (SEQ. ID NO.: 1) |
| 2 | W | M | A | R | I | T | P | A | S | G | N | T | N | Y | V | D | (SEQ. ID NO.: 2) |
| 3 | W | I | S | W | I | N | Y | N | S | S | T | T | H | Y | A | D | (SEQ. ID NO.: 3) |
| 4 | W | I | A | A | I | S | P | Y | N | G | Y | T | Y | Y | V | D | (SEQ. ID NO.: 4) |
| 5 | W | V | G | G | I | S | Q | Y | S | G | D | I | C | Y | A | D | (SEQ. ID NO.: 5) |
| 6 | W | V | G | A | I | Y | S | Y | G | G | T | T | S | Y | A | D | (SEQ. ID NO.: 6) |

FIG. 1A

| Kabat # | 95 | 96 | 97 | 98 | 99 | 100 | 100a | 100b | 100c | 100d | 100e | 100f | 100g | 100h | 100i | 100j | 100k | |
|---|---|---|---|---|---|---|---|---|---|---|---|---|---|---|---|---|---|---|
| Codon | GAW | KKG | THT | GAW | RSC | RSC | TMT | THT | KHT | KSG | THT | GAT | THT | VWT | GAT | THT | THT | |
| | Asp<br>Glu | Gly<br>Leu<br>Trp<br>Val | Tyr<br>Ser<br>Phe | Asp<br>Glu | Gly<br>Ser<br>Ala<br>Thr | Ser<br>Gly<br>Ala<br>Thr | Tyr<br>Ser | Phe<br>Tyr<br>Ser | Val<br>Tyr<br>Ser<br>Ala<br>Asp<br>Phe | Gly<br>Ala<br>Trp<br>Ser | Tyr<br>Phe<br>Ser | Asp | Tyr<br>Phe<br>Ser | Asn<br>Ile<br>Phe<br>Tyr | Asp | Phe<br>Tyr<br>Ser | Tyr<br>Phe<br>Ser | |
| Initial library members | | | | | | | | | | | | | | | | | | |
| 1 | E | G | F | E | G | S | Y | S | D | A | F | D | S | I | D | Y | F | (SEQ. ID NO.: 7) |
| 2 | E | V | F | E | T | S | Y | Y | A | A | F | D | S | F | D | S | S | (SEQ. ID NO.: 8) |
| 3 | E | V | S | E | S | T | S | Y | Y | S | S | D | Y | F | D | S | S | (SEQ. ID NO.: 9) |
| 5 | E | W | S | E | A | S | Y | S | F | S | Y | D | Y | N | D | F | S | (SEQ. ID NO.: 10) |
| 6 | E | G | Y | E | T | G | S | S | A | W | S | D | F | I | D | Y | S | (SEQ. ID NO.: 11) |
| 7 | D | V | S | D | G | S | S | S | S | A | Y | D | Y | N | D | S | S | (SEQ. ID NO.: 12) |
| 8 | E | W | S | E | T | T | S | S | V | A | S | D | S | Y | D | Y | Y | (SEQ. ID NO.: 13) |
| 10 | D | L | S | E | | | | | | | F | | | | | F | | (SEQ. ID NO.: 14) |

| Kabat # | 89 | 90 | 91 | 92 | 93 | 94 | 95 | 96 | 97 | 98 | 99 | 100 | |
|---|---|---|---|---|---|---|---|---|---|---|---|---|---|
| Codon | CWK | BMA | BHT | DMT | RVC | WHT | HYA | NHT | DYT | TTT | GGT | CAG | |
| Initial library members | Gln His Leu | Gln Ser Ala Glu Pro | His Tyr Ala Asp Leu Phe Pro Ser Val | Tyr Asp Asn Ala Ser Thr | Thr Ser Asn Asp Gly Ala | Thr Ser Tyr Phe Asn Ile | Pro Leu Ser Ile Thr | Pro Tyr Leu Ala Asn Asp His Ile Phe Ser Thr Val | Thr Val Ile Phe Ala Ser | Phe | Gly | Gln | |
| 1 | Q | S | A | D | A | Y | T | S | T | F | G | Q | (SEQ. ID NO.: 15) |
| 2 | Q | S | L | A | N | F | I | S | A | F | G | Q | (SEQ. ID NO.: 16) |
| 3 | Q | A | L | Y | N | N | L | V | S | F | G | Q | (SEQ. ID NO.: 17) |
| 4 | L | Q | Y | N | T | I | L | L | F | F | G | Q | (SEQ. ID NO.: 18) |

300

302 — producing a formulation including one or more proteins

304 — contacting the formulation with one or more antibodies, or antigen-binding fragment thereof, that specifically binds to one or more protein aggregates comprising fibrils relative to monomers 306 — identifying binding of the one or more antibodies to the formulation to determine the level of aggregates in the formulation 308 — administering the formulation to a subject if no binding is identified

FIG. 3A

METHODS AND SYSTEMS FOR DETECTING PEPTIDE AGGREGATES

CROSS REFERENCE TO RELATED APPLICATION(S)

This application claims the benefit of U.S. Provisional Application Nos. 62/827,496, filed Apr. 1, 2019, which is incorporated by reference as if disclosed herein in its entirety.

INCORPORATION OF SEQUENCE LISTING

The contents of the text file named "Sequences_final.txt", which was created on Jul. 21, 2023 and is 5.26 KB is size, are hereby incorporated by reference in their entireties.

BACKGROUND

There is wide-spread interest in using biologics, ranging from relatively small peptide hormones to large monoclonal antibodies, as drugs, particularly due to their unique properties, such as high affinity and specificity for their targets and low toxicity and immunogenicity. In the area of polypeptide therapeutics, the glucose-regulated peptide glucagon has proven to be a valuable therapeutic agent that modulates blood glucose levels. Glucagon is produced through the tissue-specific post-translational processing of preproglucagon. Glucagon is a first-line treatment in addressing extreme hypoglycemia, among other indications. It stimulates glycogenolysis and gluconeogenesis via binding to the glucagon receptor, resulting in a signal cascade that rapidly increases blood sugar levels. The important biological role of this peptide has led to its use for the treatment of extreme hypoglycemia in the clinic, and has made glucagon a molecule of interest (alongside insulin) for development of bihormonal pumps that manage blood sugar levels in individuals with type 1 diabetes.

A key challenge in developing biologics as therapeutics is that they display variable and difficult-to-predict levels of aggregation, which can lead to the presence of aggregated species in the purified and formulated drug product. For highly aggregation-prone biologics, concerns regarding batch-to-batch variability in drug quality and immunogenicity can greatly complicate the downstream stages of process development and quality assurance, while also presenting threats to patient safety. Indeed, native glucagon is well-known for displaying poor solubility and high propensity for aggregation into amyloid fibrils of diverse morphologies. For instance, fibril formation can occur rapidly, and its rate is highly dependent on the initial concentration of glucagon amyloid present in the sample. Consequently, reconstituted glucagon is generally only stable over short timeframes and must be solubilized immediately before use. Such challenges have led to significant efforts in optimizing formulations to minimize aggregation, enhancing peptide stability and solubility through alterations in amino acid or chemical composition, and developing assays that detect aggregates (or the propensity to form aggregates) using fluorescent dyes, intrinsic tryptophan fluorescence, and other techniques.

Despite this important progress, it remains extremely challenging to sensitively detect endogenous glucagon aggregates that are present at extremely low levels.

SUMMARY

Some embodiments of the disclosed subject matter are directed to a composition comprising one or more antibodies, or antigen-binding fragments thereof, that specifically bind to one or more protein aggregates comprising fibrils relative to monomers, wherein the one or more protein aggregates include glucagon, liraglutide, or combinations thereof. In some embodiments, the one or more antibodies include a single-chain variable fragment (scFv).

In some embodiments, the one or more antibodies include one or more heavy chain variable regions, the one or more heavy chain variable regions including a sequence $X_1X_2X_3X_4X_5X_6X_7X_8X_9X_{10}X_{11}X_{12}X_{13}X_{14}$ adhering to the following sequence definition: $X_1$ is an amino acid selected from valine, methionine, and isoleucine; $X_2$ is an amino acid selected from glycine, serine, alanine, and cysteine; $X_3$ is an amino acid selected from arginine, tryptophan, glycine, valine, serine, alanine, leucine, methionine, and threonine; $X_4$ is isoleucine; $X_5$ is an amino acid selected from tryptophan, serine, asparagine, and threonine; $X_6$ is an amino acid selected from proline, tyrosine, serine, alanine, aspartic acid, and histidine; $X_7$ is an amino acid selected from threonine, serine, aspartic acid, tyrosine, asparagine, alanine, cysteine, and glycine; $X_8$ is an amino acid selected from asparagine, glycine, serine, and aspartic acid; $X_9$ is an amino acid selected from glycine and serine; $X_{10}$ is an amino acid selected from tyrosine, serine, asparagine, threonine, aspartic acid, and alanine; $X_{11}$ is an amino acid selected from threonine and isoleucine; $X_{12}$ is an amino acid selected from arginine, tyrosine, asparagine, aspartic acid, cysteine, glycine, histidine, and serine; $X_{13}$ is tyrosine; and $X_{14}$ is an amino acid selected from alanine and valine.

In some embodiments, the one or more antibodies include one or more heavy chain variable regions, the one or more heavy chain variable regions including a sequence $X_1X_2X_3X_4X_5X_6X_7X_8X_9X_{10}X_{11}X_{12}X_{13}X_{14}X_{15}X_{16}X_{17}$ adhering to the following sequence definition: $X_1$ is an amino acid selected from aspartic acid and glutamic acid; $X_2$ is an amino acid selected from glycine, leucine, tryptophan, and valine; $X_3$ is an amino acid selected from tyrosine, serine, and phenylalanine; $X_4$ is an amino acid selected from aspartic acid and glutamic acid; $X_5$ is an amino acid selected from glycine, serine, alanine, and threonine; $X_6$ is an amino acid selected from glycine, serine, alanine, and threonine; $X_7$ is an amino acid selected from tyrosine and serine; $X_8$ is an amino acid selected from phenylalanine, tyrosine, and serine; $X_9$ is an amino acid selected from valine, tyrosine, serine, alanine, aspartic acid, and phenylalanine; $X_{10}$ is an amino acid selected from glycine, alanine, tryptophan, and serine; $X_{11}$ is an amino acid selected from tyrosine, phenylalanine, and serine; $X_{12}$ is aspartic acid; $X_{13}$ is an amino acid selected from tyrosine, phenylalanine, and serine; $X_{14}$ is an amino acid selected from asparagine, isoleucine, phenylalanine, and tyrosine; $X_{15}$ is aspartic acid; $X_{16}$ is an amino acid selected from tyrosine, phenylalanine, and serine; and $X_{17}$ is an amino acid selected from tyrosine, phenylalanine, and serine.

In some embodiments, the one or more antibodies include one or more light chain variable regions, the one or more light chain variable regions including a sequence $X_1X_2X_3X_4X_5X_6X_7X_8X_9$ adhering to the following sequence definition: $X_1$ is an amino acid selected from glutamine, histidine, and leucine; $X_2$ is an amino acid selected from glutamine, serine, alanine, glutamic acid, and proline; $X_3$ is an amino acid selected from histidine, tyrosine, alanine, aspartic acid, leucine, phenylalanine, proline, serine, and valine; $X_4$ is an amino acid selected from tyrosine, aspartic acid, asparagine, alanine, serine and threonine; $X_5$ is an amino acid selected from threonine, serine, asparagine, aspartic acid, glycine, and alanine; $X_6$ is an amino acid selected from threonine, serine, tyrosine, phenylalanine, asparagine, and isoleucine; $X_7$ is an amino acid selected from proline, leucine, serine, isoleucine, and threonine; $X_8$ is an amino acid selected from proline, tyrosine, leucine, alanine, asparagine, aspartic acid, histidine, isoleucine, phenylalanine, serine, threonine, and valine; and $X_9$ is an amino acid selected from threonine, valine, isoleucine, phenylalanine, alanine, and serine.

Some embodiments of the present disclosure are directed to a method of manufacturing one or more antibodies, or antigen-binding fragments thereof, that specifically binds to one or more protein aggregates comprising fibrils relative to monomers, including producing a formulation including one or more proteins, contacting the formulation with one or more antibodies, or antigen-binding fragments thereof, that specifically binds to one or more protein aggregates comprising fibrils relative to monomers, and identifying binding of the one or more antibodies to the formulation to determine the level of aggregates in the formulation. In some embodiments, the protein is a therapeutic protein or peptide. In some embodiments, the formulation includes a storage formulation. In some embodiments, the method includes administering the formulation to a subject if no binding is identified. In some embodiments, contacting the formulation with one or more antibodies, or antigen-binding fragment thereof includes immobilizing the formulation on a solid support, and contacting antibody-aggregate complexes with at least a second antibody comprising a detectable label. In some embodiments, the solid support is pre-treated with a globular protein prior to contacting with the formulation.

Some embodiments of the present disclosure are directed to a method for identifying one or more antibodies which bind preferentially to a protein in aggregate form compared with a monomeric form, the method including (a) performing one or more negative screens of an antibody library against a monomeric form of the protein, (b) performing one or more positive screens of the antibody library against aggregate forms of the protein, and (c) repeating steps (a) and (b), whereby one or more antibodies are identified that bind to the protein in aggregate form with high affinity and bind to monomers of the same protein with low affinity. In some embodiments, the protein is glucagon, liraglutide, or amyloid beta. In some embodiments, the antibody library is a yeast display library.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein:

FIGS. 1A-1C are charts including sequence data for antibodies according to some embodiments of the present disclosure;

FIG. 3A is a chart of a method of manufacturing an antibody according to some embodiments of the present disclosure;

DETAILED DESCRIPTION

Figure 2:
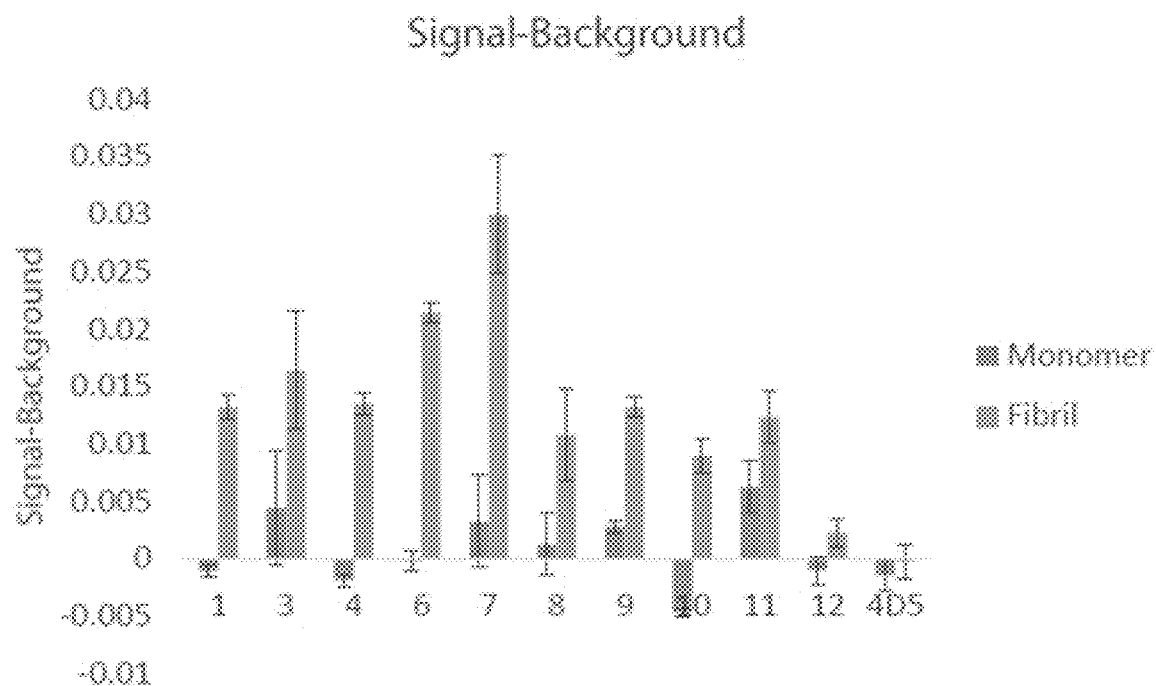
FIG. 2 is a chart showing the preferential binding to a protein in aggregate form compared with a monomeric form of antibodies according to some embodiments of the present disclosure.

The present disclosure is predicated, at least in part, on the discovery of antibodies that recognize amyloid fibrils of proteins such as glucagon and liraglutide with high conformational specificity and improve the detection of aggregates using fast, simple, and reproducible methods (e.g., ELISA or other immunoassay techniques). The assay methods described herein are more sensitive than conventional methods for detecting protein aggregates and do not require agitation to amplify pre-existing aggregates. In addition, the detection of protein aggregates using the antibodies and methods described herein can be enhanced by, for example, pretreating ELISA plates with globular proteins during antigen immobilization to greatly improve assay sensitivity. As such, the antibodies and methods provided herein may be readily integrated into the drug development process to improve the generation of safe and potent peptide therapeutics and used as a diagnostic tool for detecting misfolded proteins associated with several neurodegenerative diseases.

In this regard, the disclosure provides an antibody, or antigen-binding fragment thereof, that specifically binds to one or more protein aggregates. The term "immunoglobulin" or "antibody", as used herein, refers to a protein that is found in blood or other bodily fluids of vertebrates, which is used by the immune system to identify and neutralize foreign objects, such as bacteria and viruses. In one embodiment, an immunoglobulin or antibody is a protein that includes at least one complementarity determining region (CDR). The CDRs form the "hypervariable region" of an antibody, which is responsible for antigen binding. A whole immunoglobulin typically includes four polypeptides: two identical copies of a heavy (H) chain polypeptide and two identical copies of a light (L) chain polypeptide. Each of the heavy chains contains one N-terminal variable (VH) region and three C-terminal constant (CH1, CH2, and CH3) regions, and each light chain contains one N-terminal variable (VL) region and one C-terminal constant (CL) region. The light chains of antibodies can be assigned to one of two distinct types, either kappa (κ) of lambda (k), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The VH and VL regions have the same general structure, with each region including four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the R sheets that provide the structural framework of the variable region.

The framework regions are connected by the three CDRs. As discussed above, the three CDRs, known as CDR1, CDR2, and CDR3, form the "hypervariable region" of an antibody, which is responsible for antigen binding. The CDRs form loops connecting, and in some cases including part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

Any of the antibodies disclosed herein can be a whole antibody, as described herein, or antigen-binding antibody fragment. The terms "fragment of an antibody," "antibody fragment," "functional fragment of an antibody," and "antigen-binding fragment," are used interchangeably herein to mean one or more fragments of an antibody that retain the ability to specifically bind to an antigen. An antigen-binding antibody fragment may include, for example, one or more CDRs, the variable region (or portions thereof), the constant region (or portions thereof), or combinations thereof. Examples of antibody fragments include, but are not limited to: (i) a Fab fragment, which is a monovalent fragment consisting of the VL, VH, CL, and CH1 domains, (ii) a F(ab')2 fragment, which is a bivalent fragment including two Fab fragments linked by a disulfide bridge at the hinge region, (iii) a Fv fragment consisting of the VL and VH domains of a single arm of an antibody, (iv) a Fab' fragment, which results from breaking the disulfide bridge of an F(ab')2 fragment using mild reducing conditions, (v) a disulfide-stabilized Fv fragment (dsFv), and (vi) a domain antibody (dAb), which is an antibody single variable region domain (VH or VL) polypeptide that specifically binds antigen.

An antigen-binding antibody fragment may be of any size so long as the fragment binds to a target antigen or epitope. In this respect, an antigen-binding fragment of an antibody desirably includes between about 5 and 18 (e.g., about 5, 6, 7, 8, 9, 10, 11, 12, 13, 14, 15, 16, 17, 18, or a range defined by any two of the foregoing values) amino acids of either or both of the heavy and/or light chain variable regions.

In some embodiments, the antibody or antigen-binding fragment thereof desirably includes a heavy chain constant region (Fe) of any suitable class. Preferably, the antibody or antibody fragment includes a heavy chain constant region that is based upon wild-type IgG1, IgG2, or IgG4 antibodies, or variants thereof.

In some embodiments, the antibody, or antigen-binding fragment thereof, is a single chain antibody fragment. Examples of single chain antibody fragments include, but are not limited to, (i) a single chain Fv (scFv), which is a monovalent molecule consisting of the two domains of the Fv fragment (i.e., VL and VH) joined by a synthetic linker which enables the two domains to be synthesized as a single polypeptide chain, and (ii) a diabody, which is a dimer of polypeptide chains, wherein each polypeptide chain includes a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. In certain embodiments, the antibody or antigen-binding fragment thereof described herein is a single chain Fv (scFv).

The antibody or antigen-binding fragment thereof also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated VH and VL domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intra body-mediated gene inactivation can depend on the epitope to which the intrabody is directed, such as binding to the catalytic site on a target protein or to epitopes that are involved in protein-protein, protein-DNA, or protein-RNA interactions.

In other embodiments, the antibody or antigen-binding fragment thereof is an antibody conjugate. For example, the antibody or antigen-binding fragment thereof is all or part of an antibody conjugated to a peptide, a fluorescent molecule, a chemotherapeutic agent, or a combination thereof.

In some embodiments, the antibody or antigen-binding fragment thereof can be, or can be obtained from, a human antibody, a non-human antibody, or a chimeric antibody. By "chimeric" is meant an antibody or fragment thereof including both human and non-human regions. A "humanized" antibody is a monoclonal antibody including a human antibody scaffold and at least one CDR obtained or derived from a non-human antibody. Non-human antibodies include antibodies isolated from any non-human animal, such as, for example, a rodent (e.g., a mouse or rat). A humanized antibody can include one, two, or three CDRs obtained or derived from a non-human antibody.

Referring now to FIGS. 1A-1C, aspects of the disclosed subject matter include a composition including one or more antibodies, or antigen-binding fragments thereof. In some embodiments, the one or more antibodies include a single-chain variable fragment (scFv). In some embodiments, the one or more antibodies specifically or preferentially bind to one or more protein aggregates comprising fibrils relative to monomers of that protein (see, for example, FIG. 2). In some embodiments, the one or more protein aggregates include glucagon, liraglutide, or combinations thereof.

Referring again to FIGS. 1A and 1i, in some embodiments, the one or more antibodies include one or more heavy chain variable regions. As show in FIG. 1A, in some embodiments, the one or more heavy chain variable regions include a sequence $X_1X_2X_3X_4X_5X_6X_7X_8X_9X_{10}X_{11}X_{12}X_{13}X_{14}$ adhering to the following sequence definition: $X_1$ is an amino acid selected from valine, methionine, and isoleucine; $X_2$ is an amino acid selected from glycine, serine, alanine, and cysteine; $X_3$ is an amino acid selected from arginine, tryptophan, glycine, valine, serine, alanine, leucine, methionine, and threonine; $X_4$ is isoleucine; $X_5$ is an amino acid selected from tryptophan, serine, asparagine, and threonine; $X_6$ is an amino acid selected from proline, tyrosine, serine, alanine, aspartic acid, and histidine; $X_7$ is an amino acid selected from threonine, serine, aspartic acid, tyrosine, asparagine, alanine, cysteine, and glycine; $X_8$ is an amino acid selected from asparagine, glycine, serine, and aspartic acid; $X_9$ is an amino acid selected from glycine and serine; $X_{10}$ is an amino acid selected from tyrosine, serine, asparagine, threonine, aspartic acid, and alanine; $X_{11}$ is an amino acid selected from threonine and isoleucine; $X_{12}$ is an amino acid selected from arginine, tyrosine, asparagine, aspartic acid, cysteine, glycine, histidine, and serine; $X_{13}$ is tyrosine; and $X_{14}$ is an amino acid selected from alanine and valine. Exemplary sequences one or more heavy chain variable regions consistent with this sequence definition are included in in FIG. 1A. In some embodiments, the one or more heavy chain variable regions include a sequence according to SEQ. ID NO.: 1, SEQ. ID NO.: 2, SEQ. ID NO.: 3, SEQ. ID NO.: 4, SEQ. ID NO.: 5, SEQ. ID NO.: 6, or combinations thereof.

Referring now to FIG. 1B, in some embodiments, the one or more heavy chain variable regions include a sequence $X_1X_2X_3X_4X_5X_6X_7X_8X_9X_{10}X_{11}X_{12}X_{13}X_{14}X_{15}X_{16}X_{17}$ adhering to the following sequence definition: $X_1$ is an amino acid selected from aspartic acid and glutamic acid; $X_2$ is an amino acid selected from glycine, leucine, tryptophan, and valine; $X_3$ is an amino acid selected from tyrosine, serine, and phenylalanine; $X_4$ is an amino acid selected from aspartic acid and glutamic acid; $X_5$ is an amino acid selected from glycine, serine, alanine, and threonine; $X_6$ is an amino acid selected from glycine, serine, alanine, and threonine; $X_7$ is an amino acid selected from tyrosine and serine; $X_8$ is an amino acid selected from phenylalanine, tyrosine, and serine; $X_9$ is an amino acid selected from valine, tyrosine, serine, alanine, aspartic acid, and phenylalanine; $X_{10}$ is an amino acid selected from glycine, alanine, tryptophan, and serine; $X_{11}$ is an amino acid selected from tyrosine, phenylalanine, and serine; $X_{12}$ is aspartic acid; $X_{13}$ is an amino acid selected from tyrosine, phenylalanine, and serine; $X_{14}$ is an amino acid selected from asparagine, isoleucine, phenylalanine, and tyrosine; $X_{15}$ is aspartic acid; $X_{16}$ is an amino acid selected from tyrosine, phenylalanine, and serine; and $X_{17}$ is an amino acid selected from tyrosine, phenylalanine, and serine. Exemplary sequences one or more heavy chain variable regions consistent with this sequence definition are included in in FIG. 1B. In some embodiments, the one or more heavy chain variable regions include a sequence according to SEQ. ID NO.: 7, SEQ. ID NO.: 8, SEQ. ID NO.: 9, SEQ. ID NO.: 10, SEQ. ID NO.: 11, SEQ. ID NO.: 12, SEQ. ID NO.: 13, SEQ. ID NO.: 14, or combinations thereof.

In some embodiments, the one or more heavy chain variable regions include a VHCDR1 including GFNIKDT (SEQ. ID NO.: 19).

Referring now to FIG. 1C, in some embodiments, the one or more antibodies include one or more light chain variable regions. In some embodiments, the one or more light chain variable regions include a sequence $X_1X_2X_3X_4X_5X_6X_7X_8X_9$ adhering to the following sequence definition: $X_1$ is an amino acid selected from glutamine; histidine, and leucine; $X_2$ is an amino acid selected from glutamine, serine, alanine, glutamic acid, and proline; $X_3$ is an amino acid selected from histidine, tyrosine, alanine, aspartic acid, leucine, phenylalanine, proline, serine, and valine; $X_4$ is an amino acid selected from tyrosine, aspartic acid, asparagine, alanine, serine and threonine; $X_5$ is an amino acid selected from threonine, serine, asparagine, aspartic acid, glycine, and alanine; $X_6$ is an amino acid selected from threonine, serine, tyrosine, phenylalanine, asparagine, and isoleucine; $X_7$ is an amino acid selected from proline, leucine, serine, isoleucine, and threonine; $X_8$ is an amino acid selected from proline, tyrosine, leucine, alanine, asparagine, aspartic acid, histidine, isoleucine, phenylalanine, serine, threonine, and valine; and $X_9$ is an amino acid selected from threonine, valine, isoleucine, phenylalanine, alanine, and serine. Exemplary sequences one or more light chain variable regions consistent with this sequence definition are included in FIG. 1C. In some embodiments, the one or more light chain variable regions include a sequence according to SEQ. ID NO.: 15, SEQ. ID NO.: 16, SEQ. ID NO.: 17, SEQ. ID NO.: 18, or combinations thereof. In some embodiments, the one or more antibodies include a single-chain variable fragment (scFv).

In some embodiments, the one or more light chain variable regions include a VLCDR1 including RASQDVNTAVA (SEQ. ID NO.: 20). In some embodiments, the one or more light chain variable regions include a VLCDR2 including SASFLYS (SEQ. ID NO.: 21).

As discussed above, in some embodiments, the one or more antibodies, or antigen-binding fragments thereof, described herein specifically bind to one or more protein aggregates. By "preferentially bind," "specifically bind," or "binding specificity," it is meant that the antibody specifically recognizes and binds to its cognate antigen substantially greater than other antigens or proteins. Protein aggregation is a biological phenomenon in which mis-folded proteins aggregate (i.e., accumulate and clump together) either intra- or extracellularly. Protein aggregation has become a topic of growing interest in recent years in pharmaceutical research, as aggregation of protein or peptide-based therapeutics (e.g. biologics) variably occurs throughout the manufacturing process (e.g., cell culture, purification, formulation, storage, shipment, etc.). As discussed above, the batch-to-batch variability in drug quality and immunogenicity of highly aggregation-prone biologics can greatly complicate the downstream stages of bioprocess development and quality assurance, while also presenting threats to patient safety. Misfolded protein aggregates also play an important role in cell dysfunction and tissue damage, leading to a variety of diseases. For example, prion protein (Prion diseases), amyloid-beta (Alzheimer's disease), alpha-synuclein (Parkinson's disease), Huntingtin (Huntington's disease), serum amyloid A (AA amyloidosis) and islet amyloid polypeptide (Type 2 Diabetes) are some of the proteins that trigger disease when they are misfolded. In fact, protein aggregates have been implicated in a wide variety of diseases known as amyloidoses, including ALS, Alzheimer's, Parkinson's and prion disease.

Protein aggregation may manifest as fibrilization or formation of insoluble structures from completely or partially unfolded peptides. Thus, the protein aggregates described herein may also be referred to as "fibrils" or "amyloid fibrils." Generally, the term "fibrils" refers to biological structures composed of linear biopolymers. Amyloid fibrils are formed by normally soluble proteins, which assemble to form insoluble fibers that are resistant to degradation. Their formation can accompany disease, which disease is characterized by a specific protein or peptide that aggregates.

In some embodiments, the one or more protein aggregates include any protein that is capable of aggregation or fibrilization. In some embodiments, a protein aggregate includes a peptide or protein therapeutic (e.g., a biologic). Thus, in some embodiments, the antibodies and methods described herein are used to detect any suitable therapeutic peptide or protein known in the art, such as those approved for use by the U.S. Food and Drug Association (FDA), or therapeutics currently under pre-clinical or clinical development. In some embodiments, the peptide or protein is used for the treatment of metabolic disorders (e.g., glucagon, liraglutide, insulin glargine, insulin lispro, etc.), cancer (e.g., trastuzumab, rituximab, interferon beta-1a, etc.), hematologic disorders (e.g. epoetin alfa, antihemophilic factor, bivalirudin, etc.), immunological disorders (e.g., etanercept, pegtilgrastim, adalimumab, etc.), bone disorders (e.g., denosumab), cardiac disorders (e.g., bevacizumab, evolocumab), infectious diseases (e.g., interferon beta-1a, palivizumab, human rabies virus immune globulin), respiratory disorders (e.g., beractant), neurological disorders (e.g., botulinum toxin type A and B, glatiramer acetate, peginterferon beta-1a), eye disorders (e.g., ranibizumab, pegaptanib), malabsorption disorders (e g, teduglutide), and the like. In other embodiments, a protein aggregate include a protein whose aggregation and/or misfolding is associated with disease. For example, as discussed above, the protein aggregates include prion protein, amyloid-beta peptides (e.g., Aβ-40 or Aβ-42), alpha-synuclein, Huntingtin, serum amyloid A, or islet amyloid polypeptide (IAPP).

In certain embodiments, the protein aggregate include glucagon, liraglutide, or combinations thereof. Glucagon is a 29 amino acid peptide produced by the alpha cells in the pancreas by proconvertase 2 processing products of the pre-pro-glucagon gene. Classically, hypoglycemia triggers glucagon release. The main function of glucagon is to increase blood glucose. Through both glycogenolysis and increased gluconeogenesis. It also affects lipid metabolism, breaking down fat through lipolysis and increasing ketone production. Glucagon affects protein metabolism, increasing ureagenesis and causing amino acid uptake into hepatocytes. The resultant carbon skeletons can then enter the gluconeogenic pathway. Glucagon therefore acts in multiple ways to maintain fuel supply to all organs in the body. Glucagon can form several types of fibrils that differ at the level of molecular packing of the peptide. Each type forms through distinct nucleation-dependent aggregation pathways influenced by solution conditions and can be self-propagated by seeding. An increasing number of functional amyloid-like structures have been discovered in nature, and it has recently been proposed that an amyloid-like state of glucagon may be utilized by the pancreatic α-cells as in vivo storage form. Because of its high propensity for amyloid fibril formation, pharmaceutical glucagon (e.g., GLUCAGEN® HYPOKIT® (Novo Nordisk, Princeton, NJ) or GLUCAGON™ (Eli Lilly and Company, Indianapolis, IN)) is currently supplied as a powder to be dissolved in supplied water immediately before use.

Liraglutide is a long-acting analog of glucagon-like peptide-1 GLP-1 currently approved in the U.S. for the treatment of type 2 diabetes (VICTOZA®. Novo Nordisk) and for chronic weight management in obese adults (SAXENDA®, Novo Nordisk). Liraglutide (γ-glutamoyl(N-α-hexadecanoyl)-Lys,26 Arg34-GLP-1(7-37)) is an acylated derivative of mammalian GLP-1, sharing 97% sequence homology with the native peptide. It is based upon the sequence of GLP-1 (7-37), with the addition of a glutamic acid residue at position 26, allowing attachment of a palmitoyl group and a substitution (arginine instead of lysine) at position 34. The palmitoyl group facilitates non-covalent binding to albumin after injection, whereby the peptide escapes glomerular filtration. Together with self-association, this results in a pharmacokinetic profile with slow absorption ($T_m x$ of ~10-14 hours) and a half-life of around 12.5 hours after subcutaneous injection, making it suitable for once-daily administration. In clinical trials of up to 1 year duration, liraglutide has been demonstrated to have beneficial effects on islet cell function, leading to improvements in glycemic. Compared to GLP-1, liraglutide has an added fatty acid (FA) moiety that causes oligomerization of liraglutide as suggested by small-angle x-ray scattering (SAXS) and multiangle static light scattering (MALS) analysis.

Descriptions of the antibody, protein aggregates, and components thereof set forth above also are applicable to those same aspects of a method for identifying an antibody, discussed in greater detail below. In some embodiments, the protein aggregates are composed of any suitable protein with propensity to aggregate in a sample, such as those described herein or known in the art. In some embodiments, the protein aggregates are composed of glucagon, liraglutide, amyloid beta, or combinations thereof.

Figure 3B:
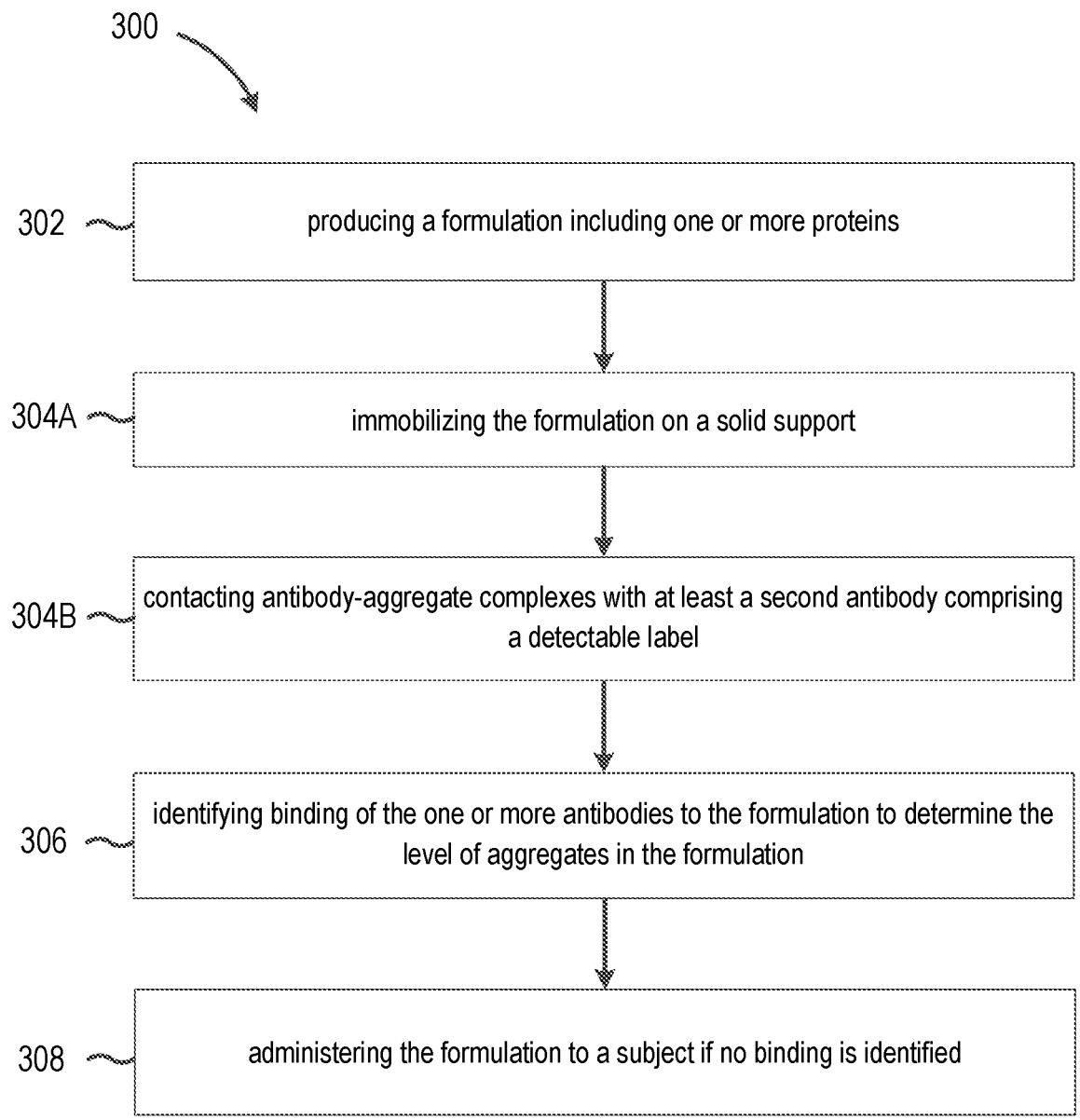
FIG. 3B is a chart of a method of manufacturing an antibody according to some embodiments of the present disclosure.

Referring now to FIGS. 3A-3B, some embodiments of the present disclosure are directed to a method 300 of manufacturing one or more antibodies, or antigen-binding fragments thereof, that specifically binds to one or more protein aggregates comprising fibrils relative to monomers as discussed above. In some embodiments, at 302, a formulation including one or more proteins is produced. In some embodiments, the formulation is a sample, e.g., of a larger product composition of which quality-control or diagnostic data is desired. In some embodiments, the protein is a therapeutic protein or peptide. In some embodiments, the formulation includes a storage formulation. At 304, the formulation is contacted with the one or more antibodies, or antigen-binding fragments thereof. Referring specifically to FIG. 3B, in some embodiments, at 304B, the formulation is immobilized on a solid support. At 304B, the antibody-aggregate complexes are contacted with at least a second antibody comprising a detectable label. In some embodiments, the solid support is pre-treated with a globular protein prior to contacting with the formulation, e.g., bovine serum albumin (BSA), ovalbumin, etc.

Any solid support known in the art can be used in the methods described herein, including but not limited to, solid supports made out of polymeric materials in the form of planar substrates or beads, and the like. For example, in some embodiments, the solid support is a slide, multi well plate, (e.g., 96-well plate), or a bead, e.g., latex, agarose, sepharose, streptavidin, tosylactivated, epoxy, polystyrene, amino bead, amine bead, carboxyl bead, etc., or combinations thereof. In certain embodiments, the bead is a particle, e.g., a microparticle. The terms "bead" and "particle" are used herein interchangeably and refer to a substantially spherical solid support. The terms "microparticle" and "microbead" are used interchangeably herein and refer to a microbead or microparticle that is allowed to occupy or settle in an array of wells, such as, for example, in an array of wells in a detection module. Any number of techniques known in the art may be used to attach a protein or peptide to a solid support, such as a plate or microparticle.

The terms "sample" and "test sample," are used interchangeably herein and refer to a substance containing or suspected of containing one or more protein aggregates of interest. The sample may be derived or obtained from any suitable source. In some embodiments, the sample is synthetic (e.g., produced in a laboratory), or a naturally-occurring substance obtained or derived from, e.g., the environment (e.g., air, soil, fluid samples, e.g., water supplies, etc.), an animal (e.g., a mammal), a plant, or another organism. In one embodiment, the sample is a drug product or preparation. In this regard, in some embodiments, the sample is any suitable drug product or preparation (e.g., composition or formulation) at any suitable stage of drug development, both pre-clinical and clinical. For example, the source of the sample is obtained during initial discovery and cell culture of the biotherapeutic, during quality testing of final formulation batches, or from batches for final product storage. In some embodiments, whatever type of sample is used in the disclosed methods, the sample includes a protein in both aggregate/fibrillar and non-aggregate (e.g., soluble) forms (i.e., a mixture).

In some embodiments, the solid support is contacted with a volume of the sample using any suitable method known in the art. The term "contacting" as used herein, refers to any type of combining action which brings a solid support into sufficiently close proximity with one or more protein aggregates in a sample such that a binding interaction will occur if one or more protein aggregates are present in the sample. Contacting may be achieved in a variety of different ways, including combining the sample with a multi well plate or microparticle. In some embodiments, the contacting is repeated as many times as necessary.

In certain embodiments, the solid support includes a protective, blocking, or passivating layer that can eliminate or minimize non-specific attachment of other components to the binding surface during the assay which may lead to false positive signals during detection or loss of signal. Examples of such materials include, but are not limited to, polymers, such as poly(ethylene glycol), that repel the non-specific binding of proteins~naturally occurring proteins with this property, such as serum albumin and casein: surfactants, e.g., zwitterionic surfactants, such as sulfobetaines; naturally occurring long-chain lipids; polymer brushes, and nucleic acids, such as salmon sperm DNA. In one embodiment, the solid support is blocked by pre-treating with a globular protein prior to contacting with the sample. For example, as discussed above, in some embodiments, the solid support is pre-treated with an acidic protein (i.e., pH 4.5-4.7), such as BSA or ovalbumin.

The second antibody including a detectable label is also referred to in the art as a "conjugate" or "secondary antibody." The term "conjugate," as used herein, refers to a complex including an antibody and a detectable label. In certain embodiments, the second antibody directly binds to the antibody portion of the antibody-aggregate complex. In other embodiments, the second antibody directly binds to the protein aggregate (e.g., such as in a sandwich immunoassay). The terms "detectable label," and "label," as used herein, refer to a moiety that can produce a signal that is detectable by visual or instrumental means. In some embodiments, the detectable label is, for example, a signal-producing substance, such as a chromogen, a fluorescent compound, an enzyme, a chemiluminescent compound, a radioactive compound, and the like. In one embodiment, the detectable label is a fluorescent compound, such as a fluorophore.

Referring again to FIGS. 3A-3B, at 306, binding of the one or more antibodies to the formulation is identified to determine the level of aggregates in the formulation. In some embodiments, at 308, the formulation is administered to a subject if no binding is identified.

The presence or amount of protein aggregates (e.g., amyloid fibrils) in a sample can be determined (e.g., quantified) using any suitable method known in the art. Such methods include, but are not limited to, immunoassays. Any suitable immunoassay may be utilized, such as, for example, a sandwich immunoassay (e.g., monoclonal-polyclonal sandwich immunoassays), immunoassay including enzyme detection (enzyme immunoassay (EIA) or enzyme-linked immunosorbent assay (ELISA)), competitive inhibition immunoassay (e.g., forward and reverse), a competitive binding assay, heterogeneous assay, and capture on the fly assay. In one embodiment, the presence or amount of protein aggregates in the sample is determined or quantified using an ELISA assay.

Figure 4:
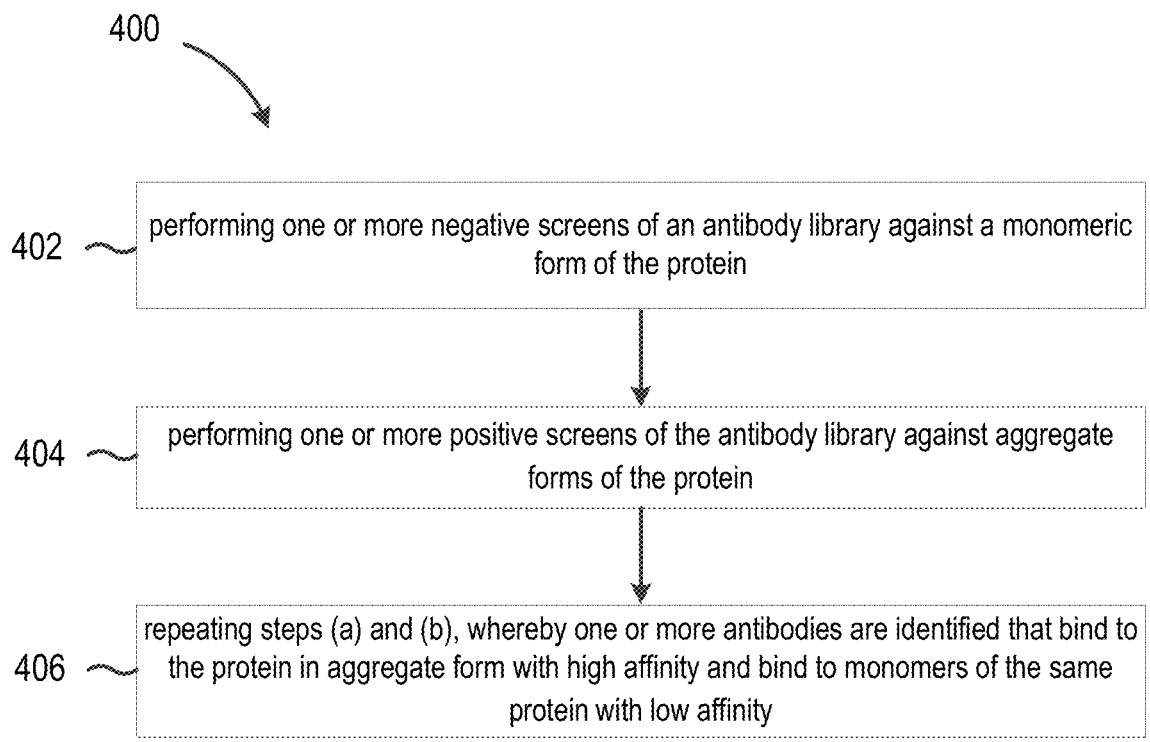
FIG. 4 is a chart of a method for screening a library to identify an antibody according to some embodiments of the present disclosure.

Referring now to FIG. 4, some embodiments of the present disclosure are directed to a method 400 for identifying one or more antibodies which bind preferentially to a protein in aggregate form compared with a monomeric form. In some embodiments, at 402, performing one or more negative screens of an antibody library against a monomeric form of the protein is performed. At 404, one or more positive screens of the antibody library against aggregate forms of the protein is performed. At 404, steps (a) and (b) are repeated, whereby one or more antibodies are identified that bind to the protein in aggregate form with high affinity and bind to monomers of the same protein with low affinity. As discussed above, in some embodiments, the protein is glucagon, liraglutide, or amyloid beta.

As used herein, the term "library" refers to a plurality of polynucleotides, proteins, or cells including a collection of two, or two or more, non-identical but related members. In an "antibody library)," each of the plurality of two or more non-identical nucleic acid sequences encode an antibody, or antigen-binding fragment thereof. Antibody libraries typically are engineered using combinatorial technologies that enable the development of in vitro immune repertoires and selection methodologies that can be used to derive antibodies with or without the direct immunization of a living host. Depending on the type of combinatorial technique used, the resulting library may be classified as an immune library, a naive library, a synthetic library, or a semi-synthetic library. "Immune libraries" are constructed from immunized donors or natural infections and typically used in biopharmaceutical research to obtain an antibody against a particular target antigen. From immune libraries, V genes of these libraries contain hypermutations and are affinity matured, and antibody fragments with monovalent dissociation constants in the nanomolar range can be isolated. "Naive libraries" are constructed from natural unimmunized human rearranged V genes, synthetic human V genes, or shuffled V genes. These universal (non-immunized) libraries differ from libraries derived from immune antibodies, in that the former are antigen-independent (i.e., a single library can be panned for specificity against virtually any antigen). In "semi-synthetic libraries" diversity is controlled by oligonucleotide synthesis, and these libraries are derived from unrearranged V-genes from pre-B cells or a single antibody framework with at least one complementary determining region (CDR) region genetically randomized. "Synthetic libraries" contain a framework region with randomly integrated codons into CDRs. Antibodies of synthetic libraries are built artificially, by in vitro assembly of V-gene segments and DJ segments. In some embodiments, V genes are assembled by introducing a predetermined level of randomization of CDR regions into germline V-gene segments, or rearranged V-genes. Synthetic libraries are antigen-independent and particularly useful for unbiased selection of antibodies against any target antigen.

Combinatorial library screening and selection methods have become a common tool for altering the recognition properties of proteins. The most widespread technique is phage display, whereby the protein of interest is expressed as a polypeptide fusion to a bacteriophage coat protein and subsequently screened by binding to immobilized or soluble biotinylated ligand. Phage display has been successfully applied to antibodies, DNA binding proteins. protease inhibitors, short peptides, and enzymes. More recently, "mammalian cell display" has been developed, which employs mammalian cells (e.g., HEK-293 cells) to display single chain antibody fragments (scFvs) for affinity maturation.

In some embodiments, the antibody library is a yeast display library. Yeast display has several advantages over phage display, including but not limited to, the antibody-antigen bond need not be broken to recover tightly-bound variants, increased library diversity due to decreased clonal deletion, and yeast cells possess secretly pathways very similar to mammalian cells.

With respect to antibody selection, the term "screening," as used herein, refers to the evaluation of an antibody library to assess suitability of a particular antibody based on particular features of interest (e.g., epitope binding and affinity). The term "selection," as used herein, refers to the separation of one or more members, such as polynucleotides, proteins (e.g., antibodies) or cells, from a library of such members. Selection can involve both detection and selection, for example where cells are selected by use of a fluorescence activated cell sorter (FACS) that detects expression of an antibody and then sorts the cells accordingly.

The term "affinity" refers to the equilibrium constant for the reversible binding of two agents and is expressed as the dissociation constant (KD). Affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (M), or from about 1 μM to about 100 μM). Antibody affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA.

Methods and systems of the present disclosure are advantageous to identify antibodies exhibiting preferential binding to protein aggregates. Antibodies according to some embodiments of the present disclosure include complementarity determining regions which are able to identify and bind to these protein aggregates even at low concentrations of aggregates and in the presence of monomeric protein. This highly sensitive but highly specific binding is effective to identify early formation of protein aggregates within what might otherwise present as a substantially pure soluble protein sample. Thus, the preferential binding exhibited by the antibodies consistent with some embodiments of the present disclosure are advantageous in numerous applications, such as in quality control of medicaments, as well as in vitro diagnostic processes.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A composition comprising one or more antibodies, or antigen-binding fragments thereof, that specifically bind to one or more protein aggregates comprising fibrils relative to monomers, wherein the one or more protein aggregates include glucagon, liraglutide, or combinations thereof,
   wherein the one or more antibodies include one or more heavy chain variable regions, wherein the one or more heavy chain variable regions include a VHCDR3 including a sequence according to SEQ. ID NO.: 7, SEQ. ID NO.: 8, SEQ. ID NO.: 9, SEQ. ID NO.: 10, SEQ. ID NO.: 11, SEQ. ID NO.: 12, SEQ. ID NO.: 13, or SEQ. ID NO.: 14, or combinations thereof, wherein the one or more heavy chain variable regions include a VHCDR2 including a sequence according to SEQ. ID NO.: 1, SEQ. ID NO.: 2, SEQ. ID NO.: 3, SEQ. ID NO.: 4, SEQ. ID NO.: 5, or SEQ. ID NO.: 6, or combinations thereof, wherein the one or more heavy chain variable regions include a VHCDR1 including GFNIKDT (SEQ. ID NO.: 19), and
   wherein the one or more antibodies include one or more light chain variable regions, the one or more light chain variable regions include a VLCDR3 including a sequence according to SEQ. ID NO.: 15, SEQ. ID NO.: 16, SEQ. ID NO.: 17, or SEQ. ID NO.: 18, or combinations thereof, wherein the one or more light chain variable regions include a VLCDR1 including RASQDVNTAVA (SEQ. ID NO.: 20) and a VLCDR2 including SASFLYS (SEQ. ID NO.: 21).

2. The composition according to claim 1, wherein the one or more antibodies include a single-chain variable fragment (scFv).

3. A method of manufacturing one or more antibodies, or antigen-binding fragments thereof, that specifically binds to one or more protein aggregates comprising fibrils relative to monomers, comprising:
   producing a formulation including one or more proteins, contacting the formulation with one or more antibodies, or antigen-binding fragments thereof, that specifically binds to one or more protein aggregates comprising fibrils relative to monomers, and
   identifying binding of the one or more antibodies to the formulation to determine the level of aggregates in the formulation,
   wherein the one or more antibodies include one or more heavy chain variable regions, wherein the one or more heavy chain variable regions include a VHCDR3 including a sequence according to SEQ. ID NO.: 7, SEQ. ID NO.: 8, SEQ. ID NO.: 9, SEQ. ID NO.: 10, SEQ. ID NO.: 11, SEQ. ID NO.: 12, SEQ. ID NO.: 13, or SEQ. ID NO.: 14, or combinations thereof, wherein the one or more heavy chain variable regions include a VHCDR2 including a sequence according to SEQ. ID NO.: 1, SEQ. ID NO.: 2, SEQ. ID NO.: 3, SEQ. ID NO.: 4, SEQ. ID NO.: 5, or SEQ. ID NO.: 6, or combinations thereof, wherein the one or more heavy chain variable regions include a VHCDR1 including GFNIKDT (SEQ. ID NO.: 19),
   wherein the one or more antibodies include one or more light chain variable regions, the one or more light chain variable regions include a VLCDR3 including a sequence according to SEQ. ID NO.: 15, SEQ. ID NO.: 16, SEQ. ID NO.: 17, or SEQ. ID NO.: 18, or combinations thereof, wherein the one or more light chain variable regions include a VLCDR1 including RASQDVNTAVA (SEQ. ID NO.: 20) and a VLCDR2 including SASFLYS (SEQ. ID NO.: 21), and
   wherein the protein is glucagon, liraglutide, or combinations thereof.

4. The method of claim 3, wherein the protein is a therapeutic protein or peptide.

5. The method of claim 3, wherein the formulation includes a storage formulation.

6. The method of claim 3, further comprising administering the formulation to a subject if no binding is identified.

7. The method according to claim 3, wherein contacting the formulation with one or more antibodies, or antigen-binding fragment thereof further comprises:
   immobilizing the formulation on a solid support; and
   contacting antibody-aggregate complexes with at least a second antibody comprising a detectable label.

8. The method according to claim 7, wherein the solid support is pre-treated with a globular protein prior to contacting with the formulation.

* * * * *

SEQUENCE LISTING

```
<160> NUMBER OF SEQ ID NOS: 21

<210> SEQ ID NO 1
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 1

Trp Ile Gly Thr Ile Asn Pro Asn Asn Ser Tyr Ile Asp Tyr Val Asp
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 2

Trp Met Ala Arg Ile Thr Pro Ala Ser Gly Asn Thr Asn Tyr Val Asp
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Trp Ile Ser Trp Ile Asn Tyr Asn Ser Ser Thr Thr His Tyr Ala Asp
1               5                   10                  15

<210> SEQ ID NO 4
<211> LENGTH: 16
<212> TYPE: PRT
<213> ORGANISM: Artificial Sequence
```

```
<220> FEATURE:
<223> OTHER INFORMATION: Synthetic Polypeptide

<400> SEQUENCE: 4

Trp Ile Ala Ala Ile Ser Pro Tyr Asn Gly Tyr Thr Tyr Tyr Val Asp
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 5

Trp Val Gly Gly Ile Ser Pro Tyr Ser Gly Asp Ile Cys Tyr Ala Asp
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 6

Trp Val Gly Ala Ile Tyr Ser Tyr Gly Gly Thr Thr Ser Tyr Ala Asp
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 7

Glu Gly Phe Glu Gly Ser Tyr Ser Asp Ala Phe Asp Ser Ile Asp Tyr
1               5                   10                  15
Phe

<210> SEQ ID NO 8
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 8

Glu Val Phe Glu Thr Ser Tyr Tyr Ala Ala Phe Asp Ser Phe Asp Ser
1               5                   10                  15
Ser

<210> SEQ ID NO 9
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 9

Glu Val Ser Glu Ser Thr Ser Tyr Tyr Ser Ser Asp Tyr Phe Asp Ser
1               5                   10                  15
Ser
```

```
<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Glu Trp Ser Glu Ala Ser Tyr Ser Phe Ser Tyr Asp Tyr Asn Asp Phe
1               5                   10                  15

Ser

<210> SEQ ID NO 11
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 11

Glu Gly Ser Glu Ala Thr Ser Ser Ala Ser Ser Asp Phe Ile Asp Tyr
1               5                   10                  15

Ser

<210> SEQ ID NO 12
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 12

Asp Val Tyr Glu Thr Gly Ser Phe Ser Trp Tyr Asp Tyr Asn Asp Ser
1               5                   10                  15

Ser

<210> SEQ ID NO 13
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 13

Glu Trp Ser Asp Gly Ser Ser Ser Ser Ala Tyr Asp Phe Asn Asp Tyr
1               5                   10                  15

Ser

<210> SEQ ID NO 14
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 14

Asp Leu Ser Glu Thr Thr Ser Ser Val Ala Ser Asp Ser Tyr Asp Phe
1               5                   10                  15

Tyr

<210> SEQ ID NO 15
<211> LENGTH: 12
<212> TYPE: PRT
```

<213> ORGANISM: Artificial Sequence
<220> FEATURE:
<223> OTHER INFORMATION: Synthetic Polypeptide

<400> SEQUENCE: 15

Gln Ser Ala Asp Ala Tyr Thr Ser Thr Phe Gly Gln
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 16

Gln Ser Leu Ala Asn Phe Ile Ser Ala Phe Gly Gln
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 17

Gln Ala Leu Tyr Asn Asn Ile Val Ser Phe Gly Gln
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 18

Leu Gln Tyr Asn Thr Ile Leu Leu Phe Phe Gly Gln
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 19

Gly Phe Asn Ile Lys Asp Thr
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 20

Arg Ala Ser Gln Asp Val Asn Thr Ala Val Ala
1               5                   10

<210> SEQ ID NO 21
<211> LENGTH: 7
<212> TYPE: PRT
<213> ORGANISM: Artificial Sequence

```
<220> FEATURE:
<223> OTHER INFORMATION: Synthetic Polypeptide

<400> SEQUENCE: 21

Ser Ala Ser Phe Leu Tyr Ser
1               5
```